United States Patent [19]

Bertaina et al.

[11] Patent Number: 4,721,812
[45] Date of Patent: Jan. 26, 1988

[54] 2,2-BIS-(2-PERFLUOROALKYLETHYLTHIO)-ACETALDEHYDES AND PROCESS FOR PRODUCTION THEREOF

[75] Inventors: Brigitte Bertaina; Aimé Cambon, both of Nice; André Lantz, Vernaison, all of France

[73] Assignee: Atochem, France

[21] Appl. No.: 46,168

[22] Filed: May 5, 1987

Related U.S. Application Data

[62] Division of Ser. No. 801,791, Nov. 26, 1985.

[30] Foreign Application Priority Data

Nov. 28, 1984 [FR] France .................. 84/18106

[51] Int. Cl.$^4$ .................. C07C 151/00; C07C 148/00
[52] U.S. Cl. ......................................... 568/41; 568/42
[58] Field of Search ...................... 568/38, 41, 50, 42

[56] References Cited

U.S. PATENT DOCUMENTS 2,461,013  2/1949  Vinton .................................. 568/41
3,937,738  2/1976  Throckmorton ...................... 568/41

Primary Examiner—Werren B. Lone
Attorney, Agent, or Firm—Brooks Haidt Haffner & Delahunty

[57] ABSTRACT

Novel 2,2-bis(2-perfluoroalkylethylthio)acetaldehydes having the formula:

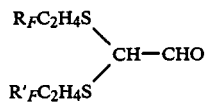

wherein $R_F$ and $R'_F$ are the same or different perfluoroalkyl groups, together with processes for producing the same and using the same to prepare surface active agents and products with hydrophobic and lipophobic properties.

4 Claims, No Drawings

2,2-BIS-(2-PERFLUOROALKYLETHYLTHIO)-ACETALDEHYDES AND PROCESS FOR PRODUCTION THEREOF

This is a division, of application Ser. No. 801,791, filed Nov. 26, 1985.

BACKGROUND OF THE INVENTION

The present invention relates to fluorinated products, and more particularly, it relates to reacting aldehydes with fluorinated thiols and the products so obtained.

Fluorinated thiols having the formula:

$$R_F-C_2H_4-SH \qquad (I)$$

wherein $R_F$ is a straight or branched perfluorinated chain, $C_nF_{2n+1}$, n being a number from one to 20, are known. These products are useful in particular as intermediates in the manufacture of surfactants or of products imparting hydrophobic and lipophobic properties to the substrates to which they are applied.

The reaction of thiols (I) with aldehydes or ketones has already been described in various patents. Thus, European patent No. 85,655 describes the preparation of aromatic thioacetals by reaction with an aromatic aldehyde or ketone according to the equation:

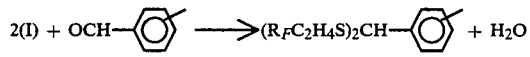

According to U.S. Pat. No. 4,239,915 and European patent No. 73,732, other thioacetals are obtained from carboxyketones, such as 4-oxopentanoic acid or from carboxyaldehydes, such as glyoxylic acid, according to the equations:

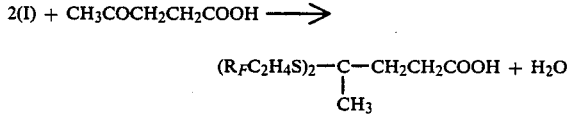

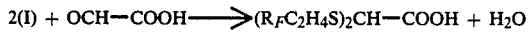

THE INVENTION

It has now been found that with glyoxal, CHO—CHO, only one aldehyde function reacts and that there are obtained the 2,2-bis-(2-perfluoroalkylethylthio)-acetaldehydes according to this invention. These correspond to the general formula:

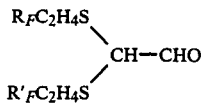

in which each of the symbols $R_F$ and $R'_F$, which are the same or different, are a perfluorinated chain, $C_nF_{2n+1}$, as defined previously. Contrary to what might have been expected, very little or no double dithioacetal (tetracondensation product) or double hemithioacetal is formed.

According to this invention, the compounds of formula (II) are prepared by reacting glyoxal with a fluorinated thiol of formula (I) or a mixture of such thiols, in the presence of an acid catalyst.

The 2-perfluoroalkylethanethiols of formula (I) are known products which can be obtained, for example, according to the methods of U.S. Pat. No. 3,544,663 by reacting thiourea with a 2-perfluoroalkylethyl iodide, ($R_FC_2H_4I$).

Glyoxal is an industrial product generally being in the form of a 30% strength aqueous solution, and this material can be used as such in the process of this invention.

Although the reaction can be carried out in the absence of a solvent, it is preferably carried out in the presence of a solvent or vehicle which is inert to the reactants. Examples of inert solvents which can be used, without being exhaustive, are aliphatic or aromatic hydrocarbons such as cyclohexane, heptane, benzene, toluene and the like; halogenated hydrocarbons such as methylene chloride, chloroform, carbon tetrachloride, 1,1,2-trifluoro-1,2,2-trichloroethane and the like; esters such as ethyl acetate and the like; ethers such as diethyl ether, tetrahydrofuran, dioxane and the like; and aliphatic acids such as acetic acid and the like. The amount of solvent can be varied within wide limits. In general, it is from 0.25 to 2.5 liters per mole of fluorinated thiol and in certain preferred embodiments, from 0.5 to 1.5 liters per mole.

The reaction is desirably carried out at a temperature from ambient temperature to 150° C.

The formation of dithioacetal requires the presence of an acid catalyst, such as, for example, hydrochloric acid, sulfuric acid, para-toluenesulfonic acid, boron trifluoride, zinc chloride and the like. The amount of catalyst can vary over wide limits. In general, the amount of catalyst used is from 0.005 to 0.5 mole per mole of thiol, and in certain preferred embodiments, it is from 0.01 to 0.1 mole.

The reaction is preferably carried out with a stoichiometric amount of the two reactants, that is to say, two moles of fluorinated thiol per mole of glyoxal. It is also possible to use excess or insufficient thiol with respect to the glyoxal.

The reaction time depends on the nature of the perfluoroalkyl group, the reaction temperature, and the nature and amount of solvent and catalyst. It can be varied from a few tens of minutes to several days. When the reaction is complete, the product can be isolated according to the usual methods, such as filtration of the reaction medium or evaporation of the solvents, and the like. If required, the reaction product can be purified by distillation, recrystallization, washing, and the like.

In the process according to the invention, it is possible to use either a pure fluorinated thiol wherein the $R_F$ group corresponds to a $C_nF_{2n+1}$ chain in which n is a well-defined integer ($R_F$=CF$_3$, C$_2$F$_5$, C$_4$F$_9$, C$_8$F$_{17}$, and the like) or a mixture of fluorinated thiols corresponding to various values of n. When it is intended to use the surfactant properties or the hydrophobic and lipophobic properties of these functional fluorinated derivatives to advantage, products or mixtures of products in which n is between 6 and 14 are preferred.

The new fluorinated compounds corresponding to the general formula (II) are valuable adjuvants which are used in the textile industry and in the leather and papermaking industries. They are particularly valuable in the manufacture of products imparting both hydrophobic and lipophobic properties to textiles, leather, paper or other substrates. These same fluorinated compounds can also be used in the preparation of fluorinated surfactants which have numerous uses as wetting or foaming agents; emulsifiers or dispersants; spreading agents for waxes, varnishes and paint; additives for lubricants and plastics; components or additives in synthetic or protein-type emulsifiers used in firefighting; and in the manufacture of emulsions of fluorocarbons in water.

All parts, percentages, proportions, and ratios herein are by weight unless otherwise stated.

The following Examples are given to illustrate embodiments of the invention as it is presently preferred to practice it. It will be understood that these Examples are illustrative, and the invention is not to be considered as restricted thereto except as indicated in the appended claims.

EXAMPLE I

A mixture of 28 g of $C_4F_9C_2H_4SH$ (0.1 mole), 9.7 g of a 30% strength aqueous solution of glyoxal (0.05 mole), 0.5 g of para-toluenesulfonic acid, and 125 ml of benzene is heated under reflux at 80° C., with continuous stirring, for 48 hours. At the end of the heating period, the reaction mixture is cooled to ambient temperature, 300 ml of water are added thereto, and the mixture is thrice extracted with 50 ml of diethyl ether. The organic phase is dried over sodium sulfate, the solvents are then evaporated off, and the residue is purified by distillation under reduced pressure.

A colorless liquid distilling at 64°-66° C. under 1 mm Hg in the amount of 22.5 g is so collected. This liquid was identified by mass-, NMR- and IR-spectrometry as 2,2-bis-(1,1,2,2-tetrahydroperfluorohexylthio)acetaldehyde:

$(C_4F_9C_2H_4S)_2CH-CHO$

The yield of the reaction is 75%.

|  | Elementary analyses | | | |
|---|---|---|---|---|
|  | C % | H % | S % | F % |
| Calculated: | 28 | 1.67 | 10.67 | 57 |
| Found: | 27.2 | 1.8 | 10.8 | 57.5 |

EXAMPLE II

Under the same conditions as those used in Example I, but employing 38 g (0.1 mole) of $C_6F_{13}C_2H_4SH$, 27.6 g of a product distilling at 89°-92° C. under 1 mm Hg is obtained and identified as 2,2-bis-(1,1,2,2-tetrahydroperfluorooctylthio)acetaldehyde:

$(C_6F_{13}C_2H_4S)_2CH-CHO$

The yield of the process is 69%.

The product is solid at ambient temperature and melts at 45°-46° C.

EXAMPLE III Using 48 g of $C_8F_{17}C_2H_4SH$ in the process of Example I, 37 g of a product identified as 2,2-bis(1,1,2,2-tetrahydroperfluorodecylthio)acetaldehyde is obtained. After recrystallization in hexane, the melting point of the product is 74°-75° C.

What is claimed is:

1. A process for the preparation of 2,2-bis-(2-perfluoroalkylethylthio)acetaldehydes having the formula:

$$\begin{array}{c} R_FC_2H_4S \\ \phantom{R_FC_2H_4S}\diagdown \\ \phantom{R_FC_2H_4S\diagdown}CH-CHO \\ \phantom{R_FC_2H_4S}\diagup \\ R'_FC_2H_4S \end{array} \quad (II)$$

wherein $R_F$ and $R'_F$ are the same or different and are a straight or branched perfluorinated chain, $C_nF_{2n+1}$, n being from one to 20, which comprises reacting a 2-perfluoroalkylethanethio or a mixture of such thiols with glyoxal in the presence of an acid catalyst.

2. A process according to claim 1 wherein the reaction is carried out in an inert solvent at a temperature from ambient temperature to 150° C.

3. A process according to claim 1 wherein glyoxal is used in the form of an aqueous solution.

4. A process according to claim 1 wherein the perfluorinated chain in the thiol or thiols contains six to 14 carbon atoms.

* * * * *